United States Patent [19]
Costanzo

[11] Patent Number: 5,873,888
[45] Date of Patent: Feb. 23, 1999

[54] SURGICAL INSTRUMENT FOR THE TRANSPLANTATION OF SELF-GROWN HAIR

[76] Inventor: Roberto Luigi Costanzo, Cso. Mediterraneo, 70, (10129) Torino, Italy

[21] Appl. No.: 911,233

[22] Filed: Aug. 15, 1997

[30]  Foreign Application Priority Data

Apr. 24, 1997  [IT]  Italy .................................. TO97A0361

[51] Int. Cl.⁶ .................................................. A61B 17/34
[52] U.S. Cl. ........................ 606/187; 606/131; 606/132; 606/185; 606/186
[58] Field of Search .................................. 606/187, 131, 606/185

[56] References Cited

U.S. PATENT DOCUMENTS

| | | | |
|---|---|---|---|
| 4,821,638 | 4/1989 | Veldman | 123/46 SC |
| 5,611,811 | 3/1997 | Goldberg | 606/187 |

*Primary Examiner*—Michael Buiz
*Assistant Examiner*—Lien Ngo

[57]  ABSTRACT

A hair transplant mechanism in which a cartridge holding numerous hair micrografts feeds a plunger mechanism. The plunger mechanism presses individual hair micrografts through a barrel to be deposited into an incision formed by a scalpel. The mechanism, using this arrangement, allows the surgeon to create an incision along a designated line and to implant the hair micrografts in a one step operation.

20 Claims, 5 Drawing Sheets

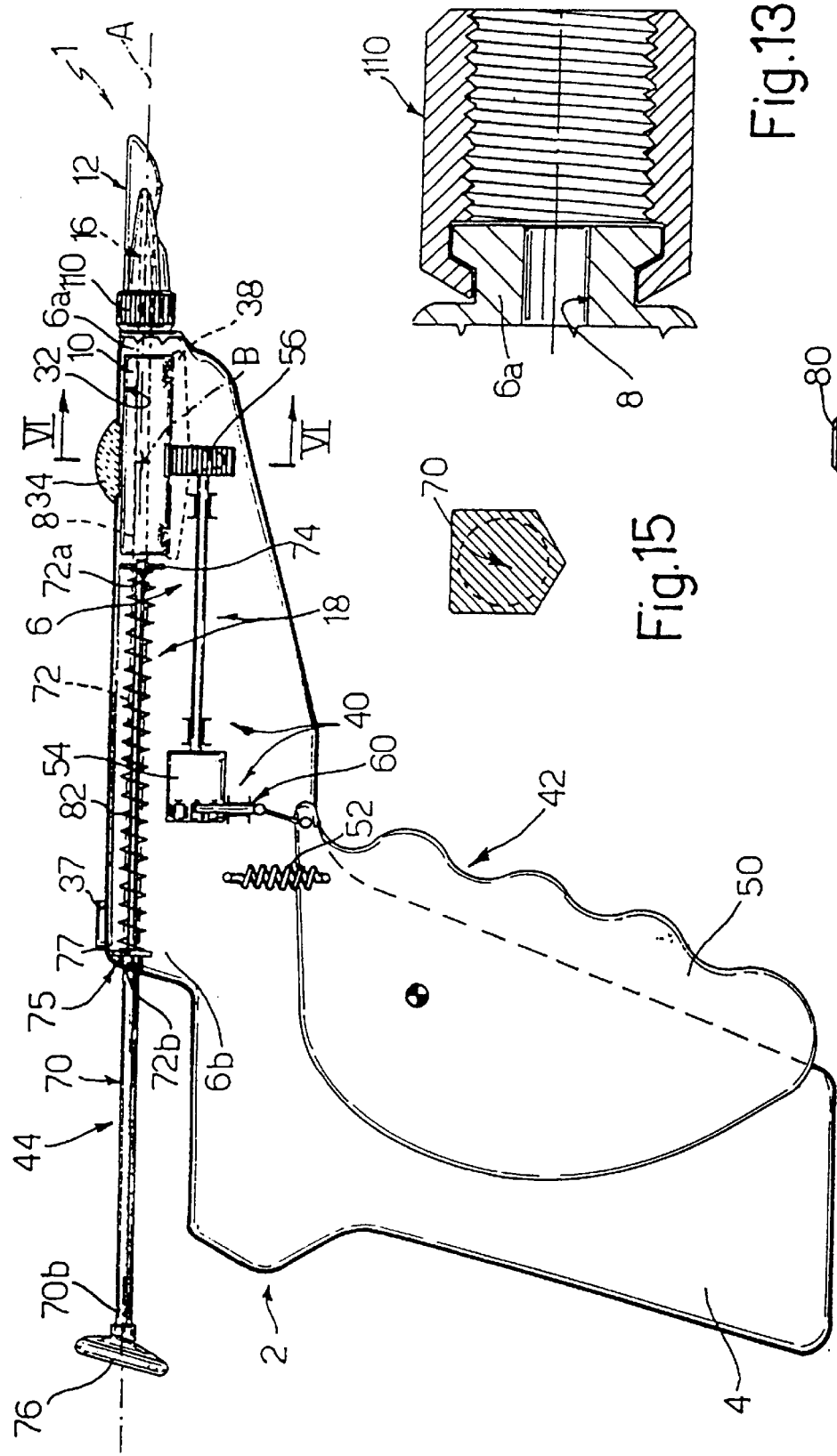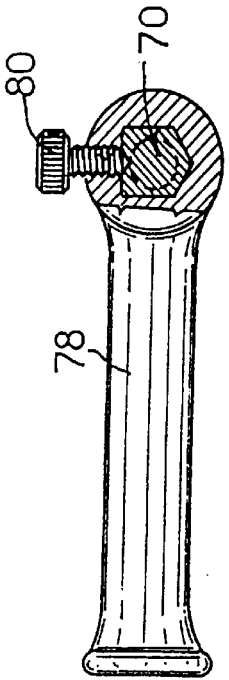

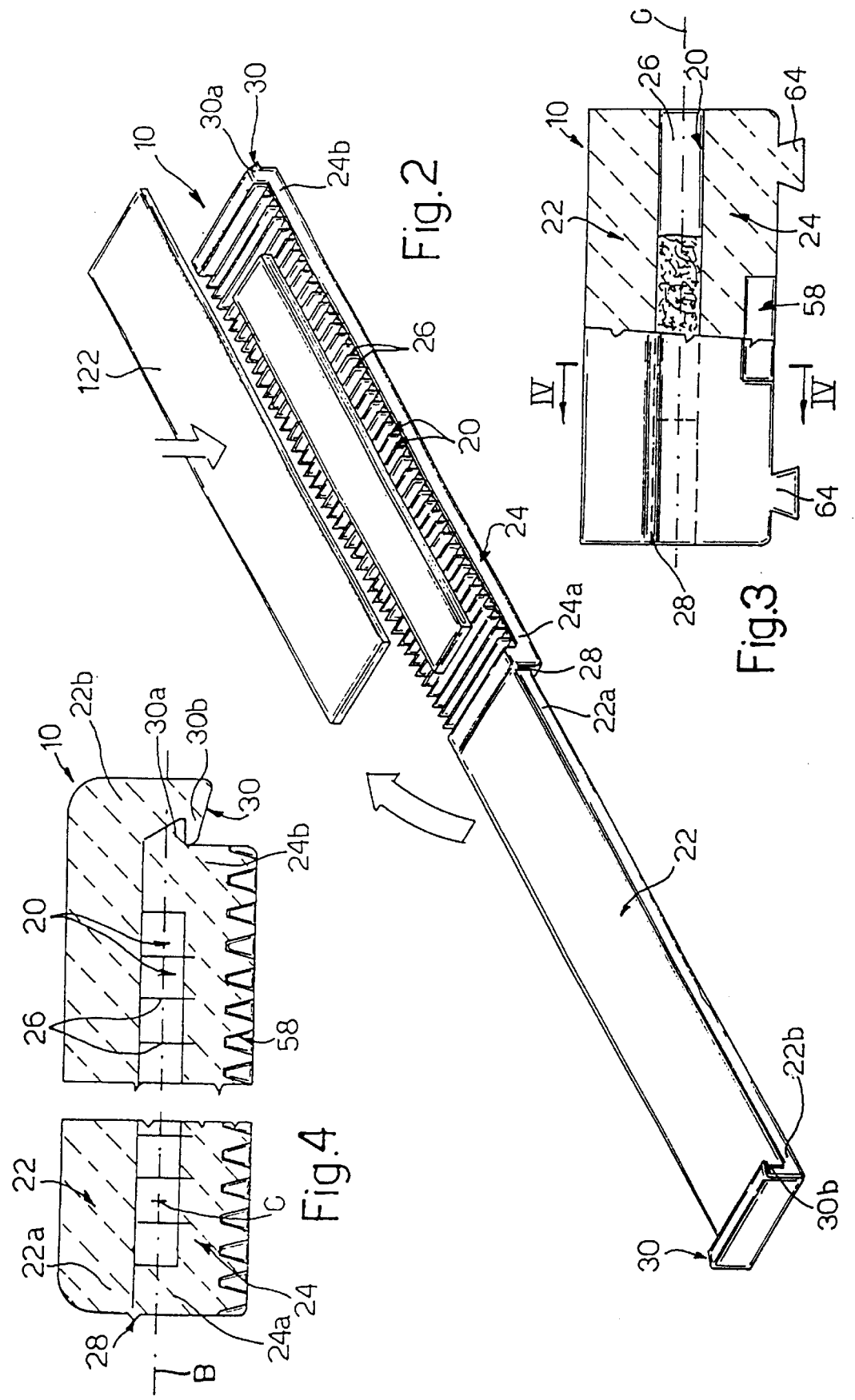

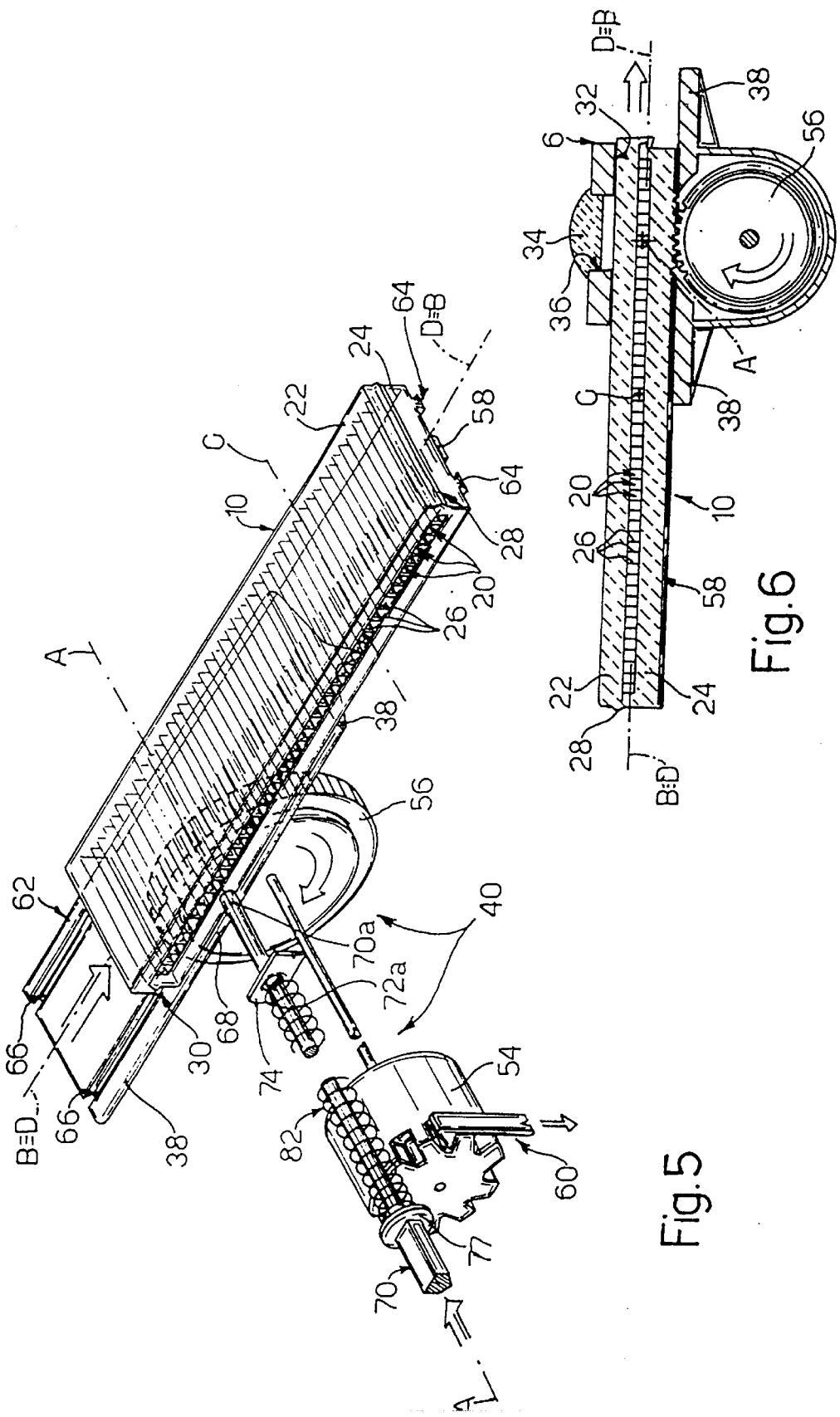

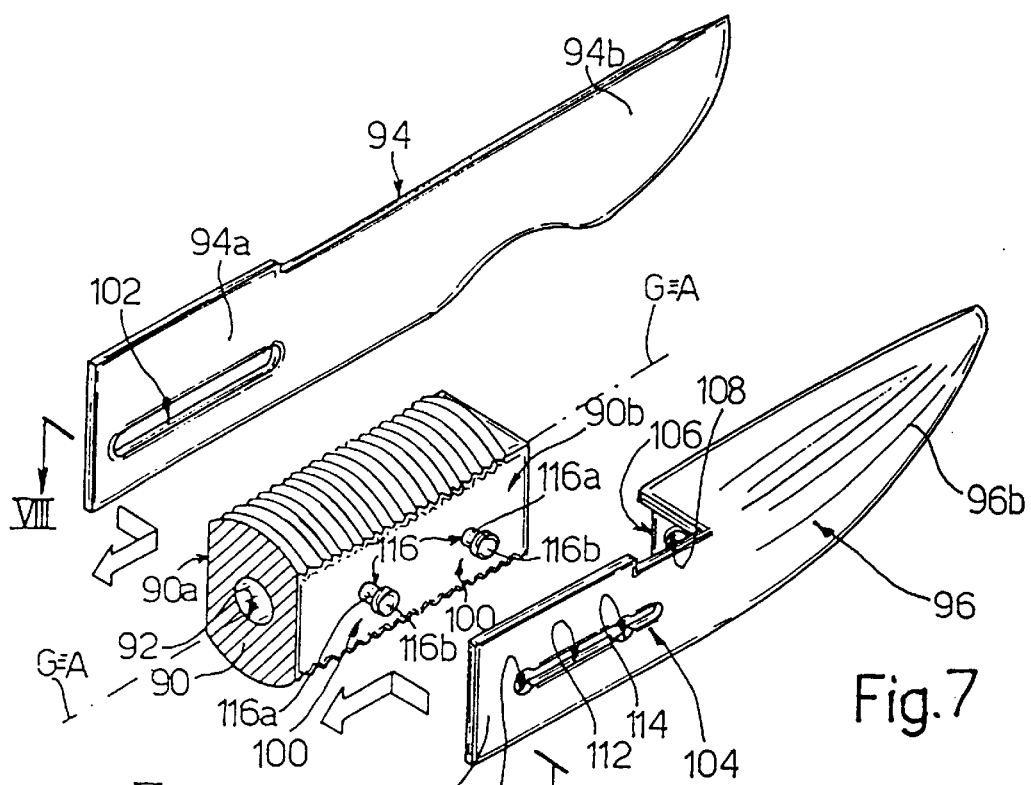
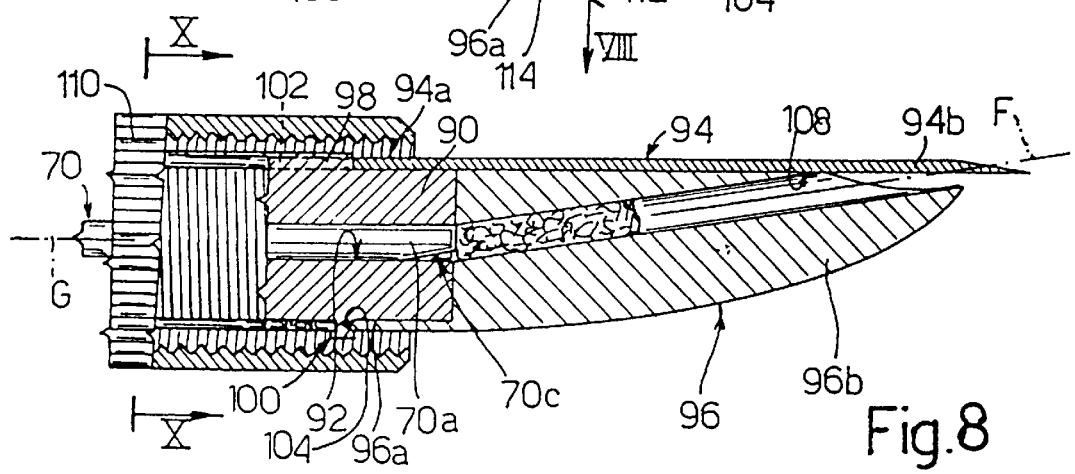
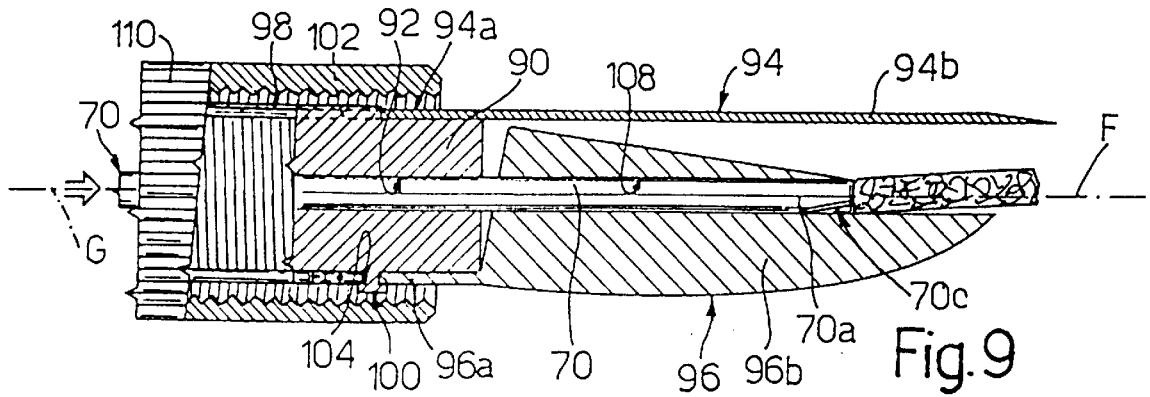

5,873,888

SURGICAL INSTRUMENT FOR THE TRANSPLANTATION OF SELF-GROWN HAIR

BACKGROUND OF THE INVENTION

Priority for this application is claimed under the Paris Convention based upon the Italian patent application filed on Apr. 24, 1997, and entitled "Strumento Chirurgico Per Il Trapianto Di Capelli Autologhi".

This invention relates to a surgical instrument for transplanting self-grown hair, i.e. hair taken from the same person undergoing the transplant.

To transplant an individual's own hair, a surgical method is employed which involves removing strips of scalp from areas of the head with hair, generally areas near the neck, manually trimming the strips of scalp using a bistro so as to obtain a plurality of micrografts, each containing one or more hair bulbs, placing the micrografts on gauze soaked in a physiologically sterile solution one by one, and inserting the micrografts into the bald area of the head one at a time. Specifically, to insert each micrografts, it is necessary to make an incision in the skin of the head by means of a bistoury, remove the micrograft from the gauze by means of a suitable tweezers, insert the micrograft into the cut and coagulate the blood which emerges from the cut.

The usual transplant procedure for self-grown hair generally requires the insertion of approximately 500 micrografts and currently requires an execution time of approximately five hours.

The execution times for hair transplant operations are currently very high indeed and necessarily require the utilization of high doses of anesthetics and analgesics and can cause a substantial loss of blood.

It is clear there is a need for an improved surgical instrument to assist in the transplanting of hair.

SUMMARY OF THE INVENTION

The scope of this invention involves the creation of a surgical instrument which allows the time necessary to perform a transplant of self-grown hair to be considerably reduced.

This invention presents a surgical instrument suitable for transplants of self-grown hair, characterized in that it is comprised of:

- a main body, substantially in the form of a pistol, comprised of a handle portion and a gun barrel portion, the inside of which defines at least one first exit channel having a longitudinal axis;
- an extractable cartridge system capable of containing a plurality of micrografts and connectable to this main body to allow for the successive loading of micrografts into the interior of this first exit channel;
- an incision and transfer system mounted to this gun barrel portion, extending in lengthwise fashion from a front end of the aforesaid gun barrel portion, having a second exit channel inside which defines an extension of the first exit channel and being capable of incising the skin by placing a cut and guiding a micrograft into the respective cut in the skin in order to graft it into the skin; and
- an actuation system mounted to the aforesaid main body and capable of pushing the micrograft which has been loaded into the first exit channel along the first and the second exit channel so as to eject it from the incision and transfer system and graft it into the skin.

To provide a better understanding of the present invention, the following describes a preferred embodiment, strictly as a non-limitative example, and referring to the enclosed drawings, in which:

The invention, together with various embodiments thereof, will explained in more detail by the accompanying drawings and following description.

DRAWINGS IN BRIEF

FIG. 1 is a schematic drawing of a surgical instrument for the transplant of self-grown hair executed in accordance with the present invention;

FIG. 2 is a perspective view of a cartridge pertaining to the instrument shown in FIG. 1;

FIG. 3 is a lateral view and partial section of the cartridge shown in FIG. 2;

FIG. 4 is a section along the plane IV—IV seen in FIG. 3;

FIG. 5 is a perspective view which schematically illustrates the advancement mechanism for the cartridge shown in FIG. 2;

FIG. 6 is a section along the plane VI—VI shown in FIG. 1;

FIG. 7 is an exploded perspective view of a first embodiment of an incision and transfer system pertaining to the instrument shown in FIG. 1;

FIG. 8 is a section along the plane VIII—VIII of FIG. 7, in which the incision system is assembled and arranged in a first operative position;

FIG. 9 is a section along the plane VIII—VIII of FIG. 7, in which the incision system is assembled and arranged in a second operative position;

FIG. 13 is a section of a connecting piece which connects the incision and transfer system to the main body of the instrument shown in FIG. 1;

FIG. 14 is a partial section view of a handgrip pertaining to the instrument shown in FIG. 1; and FIG. 15 is a cross-section of a plunger pertaining to the instrument shown in FIG. 1.

DRAWINGS IN DETAIL

Figure 10:
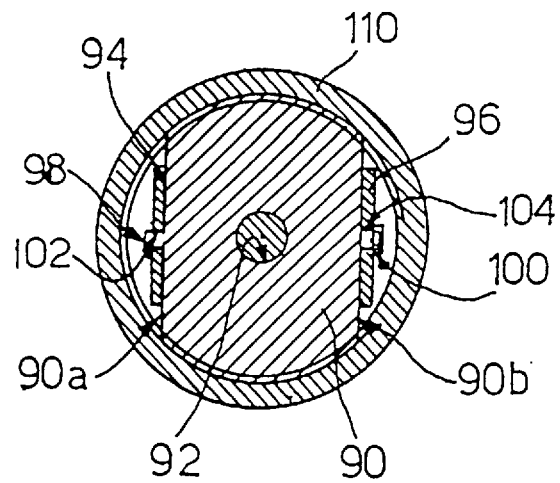
FIG. 10 is a section along the plane X—X of FIG. 8.

In FIG. 1, a numeral "1" indicates an entire surgical instrument for the transplant of self-grown hair, executed in accordance with this invention.

The surgical instrument 1 comprises a main body 2, substantially having the shape of a pistol and comprised of a handle portion 4 and a gun barrel portion 6, the inside of which defines at least a first exit channel 8 having a longitudinal axis A; an extractable cartridge 10 containing a plurality of micrografts to be implanted in the cutis of the patient undergoing the transplant and connectable to the main body 2 in the manner described in detail below, in order to arrange the micrografts one by one inside the first exit channel 8 of the gun barrel portion 6; an incision and transfer system 12, mounted on the gun barrel portion 6 extending lengthwise from a front end 6a of the said gun barrel portion 6 and having a second exit channel 16 inside which represents an extension of the first exit channel 8 and has the purpose of cutting into the cutis in order to place an incision and guiding a micrograft toward the respective incision in the cutis so as to graft it into the cutis; and an actuator system 18 mounted upon the main body 2, serving to push the micrograft arranged inside the first exit channel 8 along the first and the second exit channel 8, 16 so as to eject it from the guide system and to graft it into the cutis, and to then load another micrograft into the first exit channel 8.

As shown in FIGS. 2–4, the cartridge 10, an elongated shape oriented along its own principal axis B, has a plurality of transport compartments 20 for placing the respective micrografts, such compartments being arranged on axes C transversely to the principal axis B and flanking one another along the principal axis B.

Specifically, the cartridge 10 is substantially parallelepiped in shape and comprises a first and a second substantially rectangular wall 22, 24 of like dimensions made of transparent material for surgical use, and arranged during use so as to flank each other at a distance smaller than their length and having the longer sides parallel to the principal axis B and the smaller sides transversely to the principal axis B.

In detail, the walls 22, 24 are substantially flat, with the wall 24 moreover having opposing end portions 24a, 24b in relief, extending transversely to the principal axis B, and upon which, during use, corresponding opposing edges in the end portions 22a, 22b of the wall 22 are supported, [such edges] extending transversely to the principal axis B.

The cartridge 10 furthermore comprises a plurality of dissecting blades 26 for preparing strips of scalp, having a substantially rectangular form and mounted on the second wall 24, extending between the first and the second wall 22, 24 transversely to the principal axis B and arranged parallel to each other along the principal axis B at a predetermined distance from one another.

A pair of adjacent dissecting blades 26, in conjunction with the portions of the first and second wall 22, 24 sandwiched between them, delimits the aforesaid transport compartment 20 for placing the micrograft.

For example, utilizing a cartridge 10 having a length of approximately 10 cm and having the dissecting blades 26 at a distance of approximately 2 mm from each other, it is possible to obtain about 50 transport compartments 20 for placing the respective micrografts.

In addition, the cartridge 10 comprises a hinged connection 28 which links the first edges of the corresponding end portions 22a, 24a of the walls 22, 24, such portions being arranged transversely to the principal axis B and having the purpose of allowing for a hinged movement of the walls 22, 24 to permit the cartridge 10 to be opened and the micrografts to be inserted, as well as a spring closure 30 located at the second edges of the corresponding end portions 22b, 24b of the walls 22, 24 on opposite sides of the first edges on the end portions 22a, 24a and serving to firmly snap the facing walls 22, 24 shut, thus allowing for the spring closure of the cartridge 10.

By way of example, FIG. 4 illustrates a hinged connection 28 comprised of a thin strip of material sandwiched between the first end portion 24a in the relief of the wall 24 and the corresponding end portion 22a of the wall 22 and incorporated into the end portions 22a, 24a during the stamping of the walls 22, 24, as well as a snap closure 30 formed by a first tooth 30a at the second end portion 24b in the relief of the wall 24 and by a second tooth 30b at a corresponding end portion 22b of the wall 22 and capable of being joined to the first tooth 30a by means of snap closure.

As shown in FIGS. 5–6, the cartridge 10 is joined to the gun barrel portion 6 of the main body 2 by inserting it in a pass-through hole 32 located in the gun barrel portion 6, having an axis D oriented transversely to the longitudinal axis A of the gun barrel portion 6, intersecting the first exit channel 8 and having a substantially parallelepiped shape. Specifically, when connected, the cartridge 10 has its own principal axis B oriented orthogonally to the longitudinal axis A of the gun barrel portion 6 and parallel to the axis D of the pass-through hole 32, and the transport compartments 20 for placing the micrografts have their C axes arranged parallel to the longitudinal axis A.

In addition, the transport compartment 20 arranged inside the first exit channel 8 has its own axis C, coincidental with the longitudinal axis A.

From the two lower edges of the pass-through hole 32, there also extend transversally to the gun barrel portion 6 and parallel to the principal axis of the cartridge 10, a pair of support fins 38 serving to support the aforementioned cartridge 10 during its movement and especially when the latter has just been inserted into the pass-through hole 32 and protrudes noticeably from a part of the gun barrel portion 6, or when it has been completely emptied and must be extracted and protrudes considerably from the opposite end of the gun barrel portion 6.

To allow the user of the surgical instrument 1 a clear field of vision of the micrograft inside the first exit channel 8 and the micrografts immediately adjacent thereto, the surgical instrument 1 also comprises a magnifying lens 34 housed in a pass-through hole 36 located on an upper portion of the gun barrel portion 6 and arranged to face the segment of the first exit channel 8 engaged by the cartridge 10.

The instrument 1 is further equipped with a computation device 37 which is of known design and therefore not described in detail (it is schematically depicted in FIG. 1), arranged on the gun barrel portion 6 and serving to count the micrografts inserted into the cutis.

Referring again to FIG. 1, the actuator 18 comprises a stepwise moving device 40 by means of which the cartridge 10 advances in stepwise fashion along its principal axis B in order to regulate the transport compartments 20 which place the micrografts one by one into the first exit channel 8 and with its axis C parallel to the longitudinal axis A of the gun barrel portion 6; a control device 42 for the stepwise moving device 40; and a thrust device 44 to push the micrograft arranged inside the first exit channel 8 from the respective transport compartment 20 and along the first and the second exit channel 8, 16 so as to eject it from the incision and transfer system 12 and to graft it into the skin, as will be described in greater detail below.

The stepwise indexing device 40 and the control device 42 are both of known design and of a type commonly used in revolvers to cause the stepwise rotation of the barrel, and therefore will be briefly described here below with reference to FIGS. 1 and 5–6. In the present description, moreover, the term "step" is understood to mean the distance between each pair of C axes of the series of adjoining transport compartments 20.

As schematically illustrated in FIG. 1, the control device 42 is comprised of a trigger 50 hinging upon the handle portion 4 of the main body 2 and equipped with its own return mechanism 52 of known design—a spring in the example shown—, while the stepwise moving device 40 comprises, as schematically shown in FIGS. 1 and 5–6, a barrel 54 mounted on the main body 2 and rotating around its own fixed axis, a spool 56 rotatably attached to the main body 2 and angularly joined to the barrel 54, a track 58 (see also FIGS. 3 and 4) which engages in spool 54 and is arranged at the center of the second wall 24 of the cartridge 10 and extends along the principal axis B substantially over the entire length of the second wall 24, as well as an actuator 60 articulated to the trigger 50 and working in conjunction with the barrel 54 to rotate it in stepwise fashion with each activation of the aforementioned trigger 50.

To allow for the movement of the cartridge 10 only along its principal axis B and to prevent it from rotating around an axis orthogonal to the walls 22, 24, the surgical instrument 1 further comprises a guiding device 62, of known design, to guide the cartridge throughout its movement, and comprised, as shown in the example shown, of a pair of rectangular protrusions 64 arranged in parallel fashion, attached to the second wall 24 of the cartridge 10 and extending along the principal axis B in the proximity of the corresponding larger sides of the second wall 24, and a pair of rectangular grooves 66 arranged parallel to each other, located and extending along the support fins 38 and on a wall 68 delimiting the pass-through hole 32 and facing the protrusions 64, having a shape that complements the shape of the protrusions 64 and capable of being joined by being slipped onto the protrusions 64.

Referring now to FIGS. 1 and 5, the thrusting device 44 comprises a plunger 70 coaxially mounted to the longitudinal axis A of the gun barrel portion 6, arranged on the opposite side of the cartridge 10 relative to the incision and transfer system 12 and is partially contained within the gun barrel portion 6 of the main body 2 and partially emerges from same on the opposite side relative to the incision and transfer system 12.

Specifically, the plunger 70 is housed in its own compartment 72 coaxially with the first exit channel 8 of the gun barrel portion 6; it communicates with the first exit channel 8 through a first opening 72a located in a first back wall 74 delimiting the compartment 72; and communicates with the outside through a second opening 72b in a second back wall 75 delimiting the compartment 72 and located opposite the first back wall 74.

The plunger 70 is coaxially movable along the longitudinal axis A when activated by an external thrusting force which substantially acts along the longitudinal axis A between a position of repose, in which its first end portion 70a turns towards the cartridge 10 and is external to the transport compartment 20 arranged inside the first exit channel 8, and an operative position in which the first end portion 70a corresponds to an end segment of the second exit channel 16 pushing the micrograft arranged along the course of the plunger 70 out of the respective transport compartment 20 and along the first and second exit channel 8, 16 so as to eject it from the incision and transfer system 12 for grafting into the incision in the cutis.

The course of the plunger 70 is limited by a stop 77 seated on a segment of the plunger 70 arranged inside the compartment 72 and adjacent to the first opening 72a and serving to hit against the second back wall 75 of the compartment 72 when the plunger 70 has assumed the aforementioned operative position. In addition, the stop 77 is positioned such that the distance between the stop 77 and the first end portion 70a of the plunger 70 is equal to the distance between the position between and the first end portion 70a when the plunger 70 is in the aforementioned position of repose, and the final segment of the second exit channel 16. In this way, when the stop 77 is set to hit against the second back wall 75 of the compartment 72, the first end portion 70a of the plunger 70 has propelled the micrograft out of the incision and transfer system 12.

The external thrusting force to move the plunger 70 is manually exerted by the user of the surgical instrument 1 by pressing with the thumb of the hand to push the handle portion 4 on the second end portion 70b of the plunger 70 opposite the first end portion 70a, i.e. by depressing the free end of the plunger 70 segment which emerges from the gun barrel portion 6. To facilitate this operation, the end portion 70b of the plunger 70 is equipped with an enlargement 76 which substantially conforms to the thumb of a human hand. In an alternative embodiment, energy for driving the stepwise/indexing device 40 and plunger 70 is provided through the use of a pneumatic pressure source.

As an alternative to the enlargement 76, in order to exercise this external thrusting action, next to the second end portion 70b of the plunger 70 a handgrip 78 can be applied, as illustrated in detail in FIG. 14, which extends orthogonally to the plunger 70 and can be affixed to the plunger 70 in known fashion, such as by means of a screw 80. In this way, the user of the surgical instrument 1 can grasp the handle portion 4 with one hand and with the other activate the plunger 70 by means of the handgrip 78. The handgrip 78 can moreover be affixed to the plunger 70 in such a way that it extends from the opposite side of the plunger 70, so as to adapt to the needs of a left-handed user.

Additionally, as shown in FIG. 5 and in greater detail in FIGS. 8 and 9, the front end portion 70a of the plunger 70 has a lateral bevel 70c with a fixed orientation relative to the second exit channel 16 so as to allow, as described in greater detail below, for a smoother interaction between the first end portion 70a of the plunger 70 and the incision and transfer system 12; to keep the plunger 70 from turning around its own axis, thus changing the orientation of the lateral bevel 70c, the part of the plunger 70 inside the compartment 72 takes the form of a cylinder, as shown by a broken line in FIG. 15, to allow it to be easily inserted into the micrograft transport compartments 20, while the part of the plunger 70 emerging from the back end 6b of the gun barrel portion 6, when viewed in section, has a pentagonal profile like the opening 74, as shown by the unbroken line in FIG. 15.

The thrusting device 44 further comprises an elastic return device 82, such as a spring (FIGS. 8 and 9), seated upon the plunger 70 and working together with same in known fashion so as to exercise a reactive force opposed to the external thrusting force in order to return the plunger 70 from the operative position to the position of repose when the action of the external thrusting force is terminated.

FIGS. 7–9 show a first embodiment of the incision and transfer system 12.

The incision and transfer system 12 comprises a support piece 90 located on the front end 6a of the gun barrel portion 6 and having a first pass-through hole 92 arranged coaxially to the longitudinal axis A of the gun barrel portion 6 and defining a first segment of the second exit channel 16, as well as a first and a second blade 94, 96 extending along the longitudinal axis A from opposite side portions of the support piece 90 and bearing the attachment portions 94a, 96a of the support piece 90 and the operative portions 94b, 96b extending lengthwise beyond the support piece 90, arranged so as to touch the extension of the support piece 90 and internally defining a second segment of the second exit channel 16.

Specifically, the support piece 90 is generally cylindrical in shape and has a flat lateral surface 90a, 90b on either side, each of which carries a first engaging element 98, 100, capable of being connected to the second engaging elements 102, 104 located on the attachment portions 94a, 96a of the first and second blade 94, 96, which will be described in greater detail below.

The support piece 90 is removably connected to the front end 6a of the gun barrel portion 6 and, more specifically, the support piece 90 bears an outside thread and is connected in known fashion to a metal ring 110 (FIG. 13), in itself known and hence not described in detail, which bears an inside thread and is rotatably affixed to the front end 6a of the gun barrel portion 6 so as to turn, coaxially to the longitudinal axis A, around its own fixed axis E.

The first blade 94 is a flat blade substantially shaped like a bistoury for incising the skin, having its own attachment portion 94a affixed to a first flat lateral surface 90a of the support piece 90, and its own operative portion 94b extending fully on the extension of the attachment portion 94a, and protruding lengthwise beyond the support piece 90 and serving to make incisions into the skin of the patient.

The second blade 96 is a blade used to transfer the micrograft into the skin incision made by the first blade 94 and having its own attachment portion 96a that is substantially flat in shape and affixed to the second flat lateral surface 90b of the support piece 90 and its own operative portion 96b substantially semi-circular in shape and with a beveled edge, which protrudes lengthwise beyond the support piece 90, arranged on the extension of the support piece 90, movable by a hinge relative to the respective attachment portion 96a and serving to guide the thin micrograft into the incision in the skin made by the first blade 94 in the manner described in detail below.

In detail, the operative portion 96a of the second blade 96 has a lateral surface 106 that is turned toward the first blade 94 having a substantially flat shape and being arranged so as to touch the operative portion 94b of the first blade 94 and having a second pass-through hole 108 inside which communicates with the first pass-through hole 92 of the support piece 90 and defining a second segment of the second exit channel 16.

Additionally, the second pass-through hole 108 of the operative portion 96b of the second blade 96 has an axis F that is slanted relative to the axis G of the first pass-through hole 76 of the support piece 74 and thus inclined relative to the longitudinal axis A of the gun barrel portion 6. In detail, the F axis of the second pass-through hole 108 of the operative portion 96b of the second blade 96 is slanted toward the operative portion 94b of the first blade 94, causing its front opening with which it communicates with the exterior to be partially closed, since the operative portion 94b of the first blade 94 is arranged on the opposite side of it.

The inclination of the F axis relative to the G axis determines the detachment and separation of the second blade 96 from the first blade 94 and thus the gradual opening of the two blades when the second pass-through hole 108 is engaged by the first end portion 70a of the plunger 70 as it moves from the position of repose to the operative position.

In consequence, when the first and the second blades 94, 96 have penetrated the patient's cutis, the width of the opening of the blades 94, 96 determines the size of the incision and, under the thrust of the first end portion 70a of the plunger 70, the micrograft's fall into the incision through the front opening of the second pass-through hole 108. In fact, under the thrust of the first end portion 70a of the plunger 70, the second blade 96 detaches from the first blade 94, its F axis arranges itself coaxially to the G axis of the pass-through hole 92 and the front opening through which the pass-through hole 108 communicates with the exterior is no longer partially closed off from the operating portion 94a of the first blade 94.

The hinged movement of the operative portion 96b of the second blade 96 relative to the respective attachment portion 96a which allows the incision to be widened is achieved by making the second blade 96 of a material that is elastically deformable, so that the operative portion 96b is movable by hinge relative to the attachment portion 96a in accordance with the contact portion between the operative portion 96b and the attachment portion 96a.

The first and the second exit channel 8, 16 further share a diameter that is substantially the same and comparable to the size of the micrografts so as to prevent micrografts from becoming wedged between the plunger 70 and the walls which delimit the channels 8, 16 and becoming squeezed and damaged during the movement of the plunger 70.

By way of example, in FIG. 7 the first and the second engaging elements 98, 102 used to affix the attachment portion 94a of the first blade 94 to the respective flat lateral surface 90a consist of an elongated buttonhole-like opening located in the attachment portion 94a, and of a protrusion shaped in such a way as to complement the shape of the buttonhole-like opening, located on the flat lateral surface 90a and capable of being joined in known fashion to the buttonhole-like opening, while the first and the second engaging elements 100, 104 for fastening the attachment portion 96a of the second blade 96 to the respective flat lateral surface 90b are comprised of an elongated buttonhole-like opening 112 located in the attachment portion 96a provided with a pair of hole enlargements 114 placed at a preset distance, and a pair of pins 116, each having a main body 116a extending orthogonally from the flat lateral surface 90b and a broadened head 116b, and positioned at equidistance to the distance between the two hole enlargements 114. In this way, the second blade 96 is affixed to the support piece 90 by inserting the pins 116 inside the enlargements 114 and sliding the second blade 96 lengthwise relative to the support piece 90 in the direction indicated in the figures by arrows until the main body 116a of one of the two pins 116 abuts against one end of the buttonhole-like opening 112.

Once the blades 94, 96 are mounted on the support piece 90, this is inserted into the metal ring 110 which is rotated manually, thus screwing the support piece 90 into the metal ring 110 until one wall of the base of the support piece 90 does not abut against the gun barrel portion 6.

In practice, the user of the surgical instrument 1 initially arranges the micrografts inside the transport compartments 20 of the cartridge 10. To perform this operation the user opens the cartridge 10 as shown in FIG. 2 to spread the walls 22, 24 apart, places a strip of scalp 120 on the dissecting blades 26, lays a rectangular element 122 made of silicone material for medical use on top of the strip of scalp 120, exercises a compressive action upon this rectangular element 122 causing the strip of scalp to be dissected into a plurality of micrografts, each of which becomes lodged inside one of the transport compartments 20 as it falls; the user then removes the rectangular element 122, returns the walls 22, 24 to a position facing each other and closes the cartridge 10 by snapping it shut.

The user then inserts the cartridge 10 into the pass-through hole 32 located in the gun barrel portion 6 so that the spool 56 engages the track 58 and the guiding teeth 62 engage the grooves 64.

The user then grasps the surgical instrument by the handle portion 4 and incises the patient's cutis using the first blade 94 of the incision and transfer system 12, which partially penetrates the cutis in conjunction with a portion of the second blade 96.

The user then depresses the trigger 50 repeatedly, causing the cartridge 10 to advance in stepwise fashion until a micrograft is positioned inside the first exit channel 8.

When a micrograft has been positioned inside the first exit channel 8, the user uses the thumb of his hand to push on the enlargement 76 at the second end portion 70b of the plunger 70, causing the plunger 70 to move into the first exit channel 8.

This movement causes the first end portion 70a of the plunger 70 to thrust the micrograft out of the respective transport compartment 20 and along the first and the second exit channel 8, 16 until it ejects it from the incision and transfer system 12.

Specifically, during its movement the plunger 70 engages the second pass-through hole 108 of the second blade 96 which, being slanted relative to the direction in which the plunger 70 advances, determines the gradual detachment of the operative portion 96b of the second blade 96 of the operative portion 94b of the first blade 94. In this way, the operative portion of the second blade 96 expands the incision in the cutis and allows the micrograft to be inserted.

The lateral bevel 70c of the first end portion 70a of the plunger 70 is located on a segment of the first end portion 70a opposite the first blade 94 and has a substantially parallel slant toward the F axis of the second pass-through hole 108. In this way, at the entrance of the second pass-through hole 108, this bevel 70c glides on the initial segment of the wall delimiting the second pass-through hole 108 and determines the gradual separation of the operative portion 96b of the second blade 96 [and] of the operative portion 94b of the second blade 94, thus keeping the two operative portions 94b, 96b from being opened by the tip of the plunger 70 stopping against the wall of the second pass-through hole 108 and thus keeping the tip of the plunger 70 from crushing the micrograft against the aforesaid wall.

After the operative portion 96b of the second blade 96 has moved away from the operative portion 94a of the first blade 94, the plunger 70 slips through the second pass-through hole 108 and pushes the micrograft into the cutis.

Once the micrograft has been inserted into the cutis, the user terminates the thrusting action on the plunger 70 and the latter then returns to a position of rest by means of the elastic return element 72.

The user then removes the incision and transfer system 12 from the incision in the cutis and pushes the trigger 50 to load the next micrograft into the first exit channel 8, repeating the preceding steps until the micrografts contained in the cartridge 10 are used up.

At this point, the user replaces the empty cartridge 10 with a new cartridge which has been filled in the interim and recommences the implant procedure.

Figure 12:
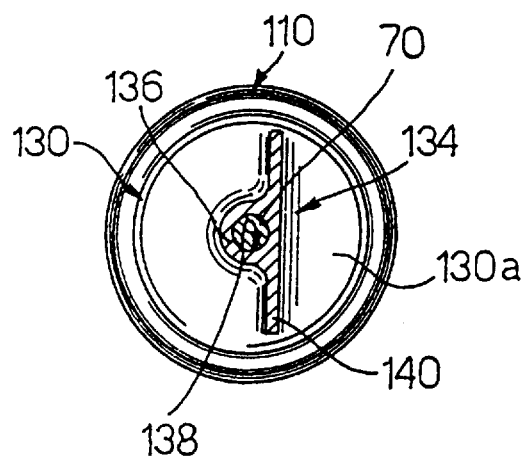
FIG. 12 is a section of plane XII—XII of FIG. 11.
Figure 11:
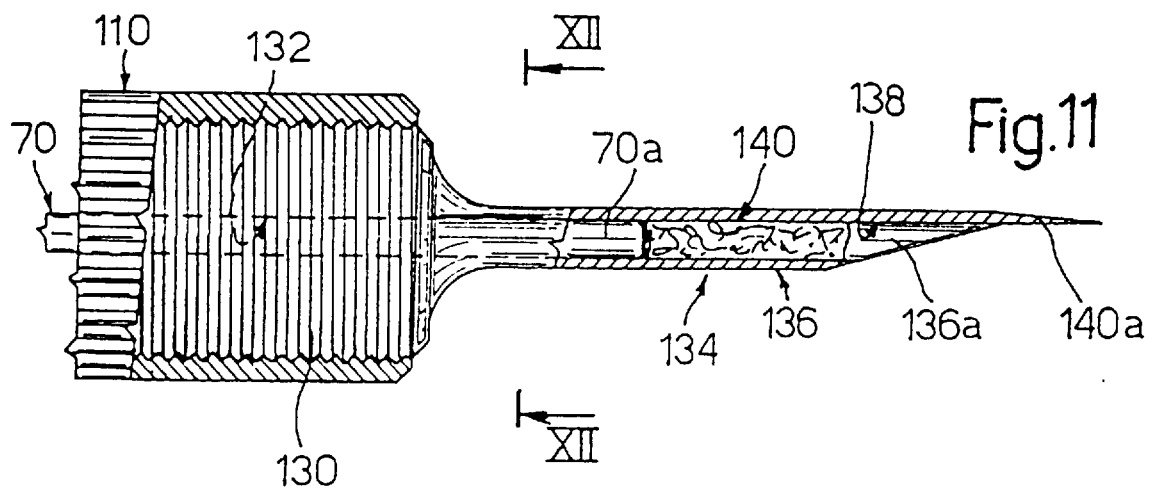
FIG. 11 is a lateral view and a partial section of a second embodiment of an incision and transfer system pertaining to the instrument shown in FIG. 1.

FIGS. 11–12 show another embodiment of the incision and transfer system 12.

In this embodiment, the incision and transfer system 12 comprises a support piece 130 located on the front end 6a of the gun barrel portion 6 and having a pass-through hole 132 coaxially to the longitudinal axis A of the gun barrel portion 6 and defining a first segment of the second exit channel 16, as well as an incision and transfer blade 134 which extends along the longitudinal axis A on the extension of the support piece 130 and internally defines a second segment of the second exit channel 16.

Specifically, the support piece 130 has a substantially cylindrical shape, has an outside thread, and is affixed to the gun barrel portion 6 in a very similar manner as that described for the support piece 90 and will therefore not be described again, while the incision and transfer blade 134 comprises a first portion 136, substantially in the shape of a tubular cylinder, extending lengthwise from one base wall 130a of the support piece 130 and having a pass-through hole 138 coaxially to the pass-through hole 132, and a second flat portion 140 substantially comprised of a bistoury blade which also extends lengthwise from the base wall 130a of the support piece 130, arranged in a tangent position and integral to the first portion 136.

The first portion 136 is shorter in length than the second portion 140 and has a free end 136a which tapers toward the free end 140a of the second portion 140.

The use of the surgical instrument 1 equipped with the incision and transfer blade 134 of the type described above is substantially similar to the one described earlier and differs from the latter only in the fact that, inasmuch as the incision and transfer blade 134 consists of a single piece, it does not offer the possibility of expanding the cut during the movement of the plunger but, in contrast to that first described for the blades 94, 96, it merely has a thrusting action to eject the micrograft.

The advantages of this surgical instrument 1 are obvious based on the above description. In fact, by using the instrument 1, the execution times necessary for hair transplants are considerably reduced, inasmuch as it is possible to make numerous successive grafts and the implant procedure can be performed rapidly using a single instrument.

Using this surgical instrument 1, therefore, a common transplant involving 500 grafts requires 30–45 minutes, rather than 5 hours as required by transplants using the commonly employed method described at the outset.

It is clearly shown that those skilled in the art will be able to make modifications and variations to the surgical instrument 1 described and illustrated here without departing from the protective scope of the present invention.

For example, a blood coagulation device of known type can be connected to the surgical instrument 1 to allow the blood emerging from the incision in which the graft has been inserted to coagulate immediately after the incision and transfer system 12 is withdrawn from the aforementioned cut.

What is claimed is:

1. A surgical instrument comprising:
    a) a cartridge adapted to hold at least two micrografts, said cartridge having,
        1) an elongated body having at least two channels, each of said channels adapted to accepted a single micrograft; and,
        2) a lid adapted to at least partially enclose said at least two channels; and,
    b) a body member adapted to be grasped by a surgeon, said body having,
        1) a barrel portion having a first end and a second end,
        2) a scalpel blade adapted to create an incision in a patient, the first end of said barrel portion positioned proximate to said scalpel blade,
        3) indexing means adapted to accept said cartridge such that one of said at least two micrografts is positioned at the second end of said barrel portion, and,
        4) a plunger mechanism adapted to press one of said at least two micrografts through said barrel portion via the second end thereof to exit into said incision.

2. The surgical instrument according to claim 1, wherein said indexing means includes means for sequentially positioning said cartridge such that each of said at least two micrografts is selectively positioned at the second end of said barrel portion.

3. The surgical instrument according to claim 2, further including operator controlled activation means for activating:
   a) said indexing means; and,
   b) said plunger mechanism.

4. The surgical instrument according to claim 3, wherein said scalpel blade is removable from said body member.

5. The surgical instrument according to claim 3, wherein said indexing means and said plunger mechanism are manually powered.

6. The surgical instrument according to claim 3, further including pneumatic means for powering said indexing means and said plunger mechanism.

7. The surgical instrument according to claim 1, wherein said cartridge includes a gear mechanism adapted to mate with said indexing means.

8. The surgical instrument according to claim 7, wherein each of said at least two channels extends perpendicularly across said elongated body.

9. The surgical instrument according to claim 8, wherein each of said at least two channels have curved walls.

10. A hair implant instrument comprising:
    a) a handle;
    b) a scalpel secured to said handle;
    c) a hair micrograft injection mechanism secured to said handle and having,
       1) a cartridge holding a hair micrograft, said cartridge having an elongated body having at least two channels, each of said channels adapted to accepted a single micrograft, and, a lid adapted to at least partially enclose said at least two channels, and,
       2) insertion means for passing said hair micrograft from said cartridge into an incision created by use of said scalpel.

11. The hair transplant instrument according to claim 10, wherein said hair micrograft injection mechanism includes:
    a) barrel portion having a first end and a second end;
    b) a plunger mechanism adapted to press said hair micrograft through said barrel portion into said incision.

12. The hair transplant instrument according to claim 11, wherein said hair micrograft injection mechanism includes indexing means for sequentially passing one of said hair micrografts in said cartridge in line with said barrel portion.

13. The hair implant instrument according to claim 12, further including, attached to said handle, operator controlled activation means for activating:
    a) said indexing means; and,
    b) said plunger mechanism.

14. The hair implant instrument according to claim 13, wherein said operator controlled activation means is adapted to transmit manually applied energy to said indexing means and said plunger mechanism.

15. The hair implant instrument according to claim 13, further including pneumatic means for powering said indexing means and said plunger mechanism in response to said activation means.

16. The hair implant instrument according to claim 10, wherein said cartridge includes a gear mechanism adapted to mate with said indexing means moving said cartridge.

17. The hair implant instrument according to claim 16, wherein each of said at least two channels extends perpendicularly across said elongated body and wherein each of said at least two channels have curved walls.

18. A surgical instrument assembly comprising:
    a) an elongated cartridge having,
       1) a base portion having at least two micrograft receiving portions, each of said micrograft receiving portions having curved walls and extending an entire width and generally perpendicular to a longitudinal axis of said base portion, each of said micrograft receiving portions having curved walls,
       2) a lid member swivel connected to said base portion and adapted to enclose an exposed side of said micrograft receiving portions,
       3) an indexing gear secured to said cartridge;
    b) a scalpel having a sharpened edge and a mounting end; and,
    c) a body member having,
       1) a handle adapted to be grasped by a surgeon,
       1) a barrel portion having a first end and a second end,
       2) a scalpel mount adapted to be secured to the mounting end of said scalpel,
       3) indexing means for cradling and indexing said cartridge such that said micrograft receiving portions are in selective communication with said barrel portion, and,
       4) a plunger mechanism adapted to selectively press one of said at least two micrografts from said cartridge through said barrel portion and into an incision created by said scalpel.

19. The assembly according to claim 18, further including a lever swivels connected to said handle portion and adapted to power said indexing means and said plunger mechanism.

20. The assembly according to claim 19, further including:
    a) pneumatic pressure means for providing pneumatic energy for operation of said indexing means and said plunger mechanism; and,
    b) pneumatic activation means for selectively communicating pneumatic energy from said pneumatic pressure means to said indexing means and said plunger mechanism.

* * * * *